Figure 1:
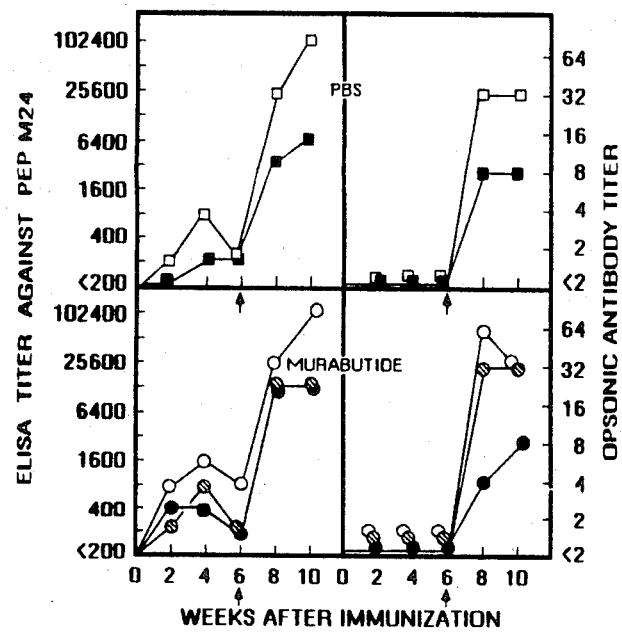

United States Patent [19]

Beachey

[11] Patent Number: 4,728,639

[45] Date of Patent: Mar. 1, 1988

[54] TYPE-SPECIFIC OPSONIC ANTIBODIES EVOKED WITH A SYNTHETIC PEPTIDE OF STREPTOCOCCAL M PROTEIN CONJUGATED TO POLYLYSINE WITHOUT ADJUVANT

[75] Inventor: Edwin H. Beachey, Memphis, Tenn.

[73] Assignee: University of Tennessee Research Corporation, Knoxville, Tenn.

[21] Appl. No.: 815,693

[22] Filed: Jan. 2, 1986

Related U.S. Application Data

[60] Continuation-in-part of Ser. No. 700,625, Feb. 12, 1985, Pat. No. 4,597,967, which is a division of Ser. No. 503,272, Jun. 12, 1983, Pat. No. 4,521,334, which is a continuation-in-part of Ser. No. 402,355, Jul. 27, 1982, Pat. No. 4,454,121.

[51] Int. Cl.$^4$ .................. A61K 37/02; C07K 7/10
[52] U.S. Cl. ........................ 514/12; 530/324; 530/402
[58] Field of Search ................ 530/324, 402; 514/12

[56] References Cited

U.S. PATENT DOCUMENTS 4,597,967  7/1986  Beachey .................. 530/324

Primary Examiner—Delbert R. Phillips
Attorney, Agent, or Firm—Weiser & Stapler

[57] ABSTRACT

A polypeptide having the formula Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-Met is conjugated to polylysine.

2 Claims, 1 Drawing Figure

TYPE-SPECIFIC OPSONIC ANTIBODIES EVOKED WITH A SYNTHETIC PEPTIDE OF STREPTOCOCCAL M PROTEIN CONJUGATED TO POLYLYSINE WITHOUT ADJUVANT

This application is a continuation-in-part of pending U.S. Application Ser. No. 700,625, filed Feb. 12, 1985, now U.S. Pat. No. 4,597,967, to Edwin H. Beachey, which is a divisional of U.S. Application Ser. No. 503,272, filed June 12, 1983 to Edwin H. Beachey now U.S. Pat. No. 4,521,334, which in turn is a continuation-in-part of U.S. Application Ser. No. 402,355, filed July 27, 1982 to Edwin H. Beachey now U.S. Pat. No. 4,454,121, all of which are incorporated herein by reference.

This invention relates to synthetic peptides of streptococcal M protein which are conjugated to polylysine which evoke type-specific opsonic antibodies in the absence of adjuvant and to pharmaceutical compositions containing them, and methods of use.

It has been established that short synthetic peptide fragments of streptococcal M protein containing as few as 13 amino acid evoke protective immunity against the related streptococci if the peptides are covalently linked to polylysine or tetanus toxoid and emulsified in complete Freund adjuvant. The need for Freund adjuvant restricts the use of such vaccines to animal studies because the toxicity of the adjuvant is too great for human use.

It is therefore an object of this invention to provide for a peptide which can evoke protective immunity without the use of adjuvant.

The brisk immune response to a single 25 nmol dose of S-CB7 linked to polylysine and emulsified in complete Freund adjuvant was reported previously (2). Without conjugation the protective immune responses to the synthetic peptide were weak even when the peptide was emulsified in complete Freund adjuvant before injection (2). It has now unexpectedly been found that when conjugated to polylysine, S-CB7 is highly immunogenic in rabbits without adjuvant.

It has now been found that unexpectedly a chemically synthesized copy S-CB7 of a fragment of 35 amino acid residues of Type 24 streptococcal M protein covalently linked to polylysine with carbodiimide and injected subcutaneously into rabbits without adjuvant raised a protective immune response (15). Although the primary immune response as measured by enzyme-linked immunosorbent assays at bi-weekly intervals was weak, the secondary responses measured by both enzyme-linked immunosorbent assays and opsonophagocytosis assays were as high as those obtained previously in rabbits immunized with the peptide conjugate emulsified in complete Freund adjuvant. Injection of murabutide, a synthetic muramyl dipeptide derivative of bacterial peptidoglycan, with the initial immunizing dose peptide conjugate had no apparent effect on the secondary immune responses.

FIG. 1 shows the immune responses with and without murabutide.

The immune response of rabbits to a synthetic peptide S-CB7 of Type 24M protein linked with carbodiimide to polylysine and injected subcutaneously in phosphate-buffered saline (PBS) alone or with an initial dose of synthetic adjuvant has been examined. The adjuvant used was a butyl derivative of muramyl dipeptide (N-acetylmuramyl-L-alanyl-D-glutamyl-n-butyl ester).

S-CB7, the chemically synthesized cyanogen bromide-derived fragment 7 of a pepsin-extracted type 24M protein (pep M24), was prepared as previously described (1, 2, 5, 10) using an automated peptide synthesizer (Beckman Intruments, Inc., Fullerton, Calif.). The synthetic peptide was purified by molecular-sieve chromatography on a column of Sephadex C-50 and further purified by high-pressure liquid chromatography (1, 5). The primary structure of S-CB7 was confirmed by quantitative amino acid analysis and by Edman degradation to the penultimate amino acid residues (3). The sequence of S-CB7 has been reported (2) as follows:

Asn-Phe-Ser-Thr-Ala-Asp-Ser-Ala-Lys-Ile-Lys-
Thr-Leu-Glu-Ala-Glu-Lys-Ala-Ala-Leu-Ala-Ala-
Arg-Lys-Ala-Asp-Leu-Glu-Lys-Ala-Leu-Glu-
Gly-Ala-Met

The purified peptide was covalently linked to polylysine with carbodiimide (2). The conjugate (25 nmol of peptide) was dissolved in PBS and injected subcutaneously behind the neck of rabbits with or without 100 ug of murabutide. Rabbit sera were collected at 2-week intervals and tested by enzyme-linked immunosorbent assays (ELISA) and opsonophagocytosis tests (1). Each of the rabbits, whether or not it received the synthetic adjuvant, showed only weak primary immune responses as measured by ELISA, but none at all as measured by the opsonization of the related type 24 streptococci during the first 6 weeks after the initial immunizing dose of peptide (FIG. 1). However, a single booster injection of an additional 25 nmol of the conjugated peptide in PBS evoked high titers of antibodies in each of the immunized rabbits in both groups (murabutide treated or untreated) as measured by both ELISA and opsonophagocytic assays (FIG. 1). The antibodies raised against the S-CB7 conjugate reacted specifically with pep M24 and S-CB7, but not with pep M5, pep M6, or pep M19. The protective activities of the antibodies elicited during the secondary immune responses were demonstrated by indirect opsonobactericidal assays (Table 1). These results demonstrate the type specificity and the protective nature of the immune responses to S-CB7.

TABLE 1

| | Indirect bactericidal tests of anti-S-CB7-polylysine against type 24 S. pyogenes[a] | | | |
|---|---|---|---|---|
| | No. of colonies of type 24 streptococci after 3-h growth in test mixtures with fresh blood from: | | | |
| Rabbit serum | Donor 1 (inoculum 11) | Donor 2 (inoculum 12) | Donor 3 (inoculum 14) | Mean ± SEM[b] |
| Preimmune (control)[c] | 7,220 | 6,840 | 6,240 | 6,767 ± 285 |
| Anti-S-CB7-polylysine in PBS | | | | |
| 8227 | 1,280 | 1,240 | 940 | 1,130 ± 95 |
| 8228 | 60 | 250 | 80 | 130 ± 60 |
| Anti-S-CB7-polylysine in PBS plus murabutide | | | | |

TABLE 1-continued

Indirect bactericidal tests of anti-S-CB7-polylysine against type 24 S. pyogenes[a]

| Rabbit serum | No. of colonies of type 24 streptococci after 3-h growth in test mixtures with fresh blood from: | | | |
|---|---|---|---|---|
| | Donor 1 (inoculum 11) | Donor 2 (inoculum 12) | Donor 3 (inoculum 14) | Mean ± SEM[b] |
| 8231 | 0 | 30 | 50 | 37 ± 15 |
| 8232 | 1,050 | 1,360 | 1,030 | 1,147 ± 107 |
| 8233 | 0 | 20 | 0 | 7 ± 7 |

[a]The test mixtures each consisted of 0.4 ml of fresh, heparinized(10 U/ml) human blood, 0.05 ml of streptococcal inoculum suspended in PBS, and 0.05 ml of preimmune or immune rabbit serum (4). After incubation at 37° C. by rotation end-over-end at 8 rpm for 3 h, blood agar pour plates were prepared from each mixture to determine growth of CFU (4).
[b]The means of each of the values obtained with each of the immune sera were significantly different (P < 0.001) from the mean value obtained with the preimmune serum pool as determined by Student's t test.
[c]The preimmune serum consisted of a pool of serum collected from each of the five rabbits (8227, 8228, 8231, 8232, and 8233) before immunization with the peptide conjugate.

FIG. 1 shows the immune responses of rabbits immunized with polylysine conjugated S-CB7 of type 24 streptococcal M protein as measured by ELISA against pep M24, a purified pepsin extract of type 24M protein (left) and by opsonic antibody assay against type 24 streptoccoci (right). Two sets of rabbits 8227 (■) and 8228 (□), 8231 (○), 8232 (●) and 8233 (○) were immunized on day zero with a subcutaneous injection of 25 nmol of polylysine-conjugated S-CB7 and PBS alone (top) or PBS supplemented with 100 ug of murabutide (bottom). At 6 weeks (arrows), all rabbits received a subcutaneously booster injection of 25 nmol of the conjugated peptide in PBS alone. In control experiments, none of the immune sera reacted in ELISA with type 5, 6 or 19M proteins extracted by limited pepsin digestion of the respective serotypes of Streptococcus pyogenes or in opsonophagocytosis tests with heterologues serotype 3, 6 or 19 streptococci, indicating the serotype specificity of the immune response.

These studies demonstrate for the first time that opsonic and bactericidal antibodies can be evoked by immunization with a chemically synthesized peptide fragment of streptococcal M protein linked to a synthetic carrier in the absence of adjuvant. Interestingly, the immune responses in the rabbits immunized with peptide conjugate in PBS alone were in the same range as those in the rabbits receiving a dose of the synthetic adjuvant, murabutide, in conjunction with the initial immunizing dose of S-CB7.

In a previous study (11), it was demonstrated that glutaraldehyde-polymerized S-CB7, but not monomeric S-CB7, was capable of evoking secondary immune responses in animals given an initial priming dose of pep M24 in PBS. Pep M24, however, is a large polypeptide fragment of $M_r$ 33,500; the intact M24 protein appears to have a molecular weight of 76,000 while that of S-CB7 is about 4,000 (4). The conjugate formed between S-CB7 and polylysine would have a minimum calculated molecular weight of 39,000. The multivalency of the S-CB7 polylysine conjugate in combination with the positive charge conferred by the polylysine probably accounts for its greater immunogenicity as compared with the monomeric form of S-CB7 (2).

The findings have bearing on the development of protective bacterial vaccines for human use. The ability to evoke protective antistreptococcal antibodies in the absence of adjuvant circumvents the potential problems arising from the use of these agents. The use of selected peptide fragments, rather than the parent molecule or even the large polypeptide fragments extracted by limited digestion with pepsin, allow disposal of a large part of the M protein molecule which may contain potentially harmful antigenic determinants giving rise to immunological cross-reactions with host tissues (7-9, 12-14). The selection of small peptide regions that contain protective epitopes shed light not only on the composition of the protective antigenic determinants of the M protein, but also on the mechanisms of acute rheumatic fever and rheumatic heart disease, the pathogenesis of which up to now has remained an enigma.

All references are incorporated herein by reference.

LITERATURE CITED

1. Beachey, E. H., J. M. Seyer, J. B. Dale, and D. L. Hasty. 1983. Repeating covalent structure and protective immunogenicity of native and synthetic polypeptide fragments of type 24 streptococcal M protein; mapping of protective and nonprotective epitopes with monoclonal antibodies. J. Biol. Chem. 258: 13250-13257.
2. Beachey, E. H., J. M. Seyer, J. B. Dale, W. A. Simpson, and A. H. Kang. 1981. Type-specific protective immunity evoked by synthetic peptide of Streptococcus pyogenes M protein. Nature (London) 292: 457-459.
3. Beachey, E. H., J. M. Seyer, and A. H. Kang. 1978. Repeating covalent structure of streptococcal M protein. Proc. Natl. Acad. Sci. USA 75: 3163-3167.
4. Beachey, E. H., G. H. Stollerman, R. H. Johnson, I. Ofek, and A. L. Bisno. 1979. Human immune response to structurally defined polypeptide fragments of streptococcal M protein. J. Exp. Med. 155: 1010-1018.
5. Beachey, E. H., A. Tartar, J. M. Seyer, and L. Chedid, 1984. Epitope-specific protective immunogenicity of chemically synthesized 13-, 18-, and 23-residue peptide fragments of streptococcal M protein. Proc. Natl. Acad. Sci. USA 81: 2203-2207.
6. Chedid, L. A., M. A. Parant, F. M. Audibert, G. J. Riveau, F. J. Parant, E. Lederer, J. P. Choay, and P. L. Lefrancier. 1982. Biological activity of a new synthetic muramyl peptide adjuvant devoid of pyrogenicity, Infect. Immun. 35: 417-424.
7. Dale, J. B., and E. H. Beachey. 1982. Protective antigenic determinant of streptococcal M protein shared with sarcolemmal membrane protein of human heart. J. Exp. Med. 156: 1165-1176.
8. Dale, J. B., and E. H. Beachey. 1985. Multiple heart cross-reactive epitopes of streptococcal M proteins. J. Exp. Med. 161: 113-122.
9. Dale, J. B., and E. H. Beachey. 1985. Epitopes of streptococcal M protein shared with cardiac myosin. J. Exp. Med. 162: 583-591.

10. Dale, J. B., J. M. Seyer, and E. H. Beachey. 1983. Type-specific immunogenicity of a chemically synthesized peptide fragment of type 5 streptococcal M protein. J. Exp. Med. 158: 1727–1732.
11. Jolivet, M., F. Audibert, E. H. Beachey, A. Tartar, H. Gras-Masse, and L. Chedid. 1983. Epitope-specific immunity elicited by a synthetic streptococcal antigen withou adjuvant. Biochem. Biophys. Res. Commun. 117: 359–366.
12. Kaplan, M. H. 1967. Multiple nature of the cross-reactive relationship beytween antigens of group A streptococci and mammalian tissue. P. 48–60. In J. J. Trentin (ed.), Crossreacting antigens and neoantigens. The Williams & Wilkins Co., Baltimore.
13. Krisher, K., and M. W. Cunningham. 1985. Myosin: a link between streptococci and heart. Science 227: 413–414.
14. Zabriskie, J. B., and E. H. Freimer. 1966. An immunological relationship between the group A streptococcus and mammalian muscle. J. Exp. Med. 124: 661.
15. Beachey, E. H.; Infection and Immunity, January 1986, pp. 362–364.

What is claimed is:

1. An immunogenic biological composition which comprises a biologically acceptable diluent and in an amount sufficient to elicit opsonic antibodies to *Streptococcus pyogenes* and not be serologically cross-reactive with tissue antigens of the heart, a polypeptide conjugae having the amino acid sequence Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-Met conjugated to polylysine.

2. A method for controlling streptococcal infections in a mammal which comprises administering to a mammal in a dose sufficient to control streptococcus pyogenes, the composition of claim 1, and controlling *Streptococcus pyogenes* in said mammal.

* * * * *